United States Patent
Fontenot et al.

(10) Patent No.: US 6,926,862 B2
(45) Date of Patent: Aug. 9, 2005

(54) CONTAINER, SHELF AND DRAWER LINERS PROVIDING ABSORBENCY AND ODOR CONTROL

(75) Inventors: Monica Carlise Fontenot, Williamsville, NY (US); Terry Pearce Ford, Woodstock, GA (US); John Wesley Fowler, Alpharetta, GA (US); Jeanette Ann Allen, Alpharetta, GA (US); Ryan Clinton Frank, Atlanta, GA (US); Gina Kay Rolsten, Lawrenceville, GA (US); Richard John Schmidt, Roswell, GA (US); Bruce Scott Williamson, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 736 days.

(21) Appl. No.: 09/871,764

(22) Filed: Jun. 1, 2001

(65) Prior Publication Data

US 2002/0182102 A1 Dec. 5, 2002

(51) Int. Cl.[7] .................................................. A61L 9/00
(52) U.S. Cl. ........................ 422/5; 422/120; 422/122; 428/68; 428/74; 428/76; 428/370; 514/58
(58) Field of Search ............................ 422/5, 120, 122; 424/76.21, 443; 514/58; 428/68, 74, 76, 370, 374

(56) References Cited

U.S. PATENT DOCUMENTS

| | | |
|---|---|---|
| 503,212 A | 8/1893 | MacLeod |
| 2,802,590 A | 8/1957 | Tupper |
| 3,638,255 A | 2/1972 | Sterrett |
| 3,849,241 A | 11/1974 | Butin et al. |
| 3,971,373 A | 7/1976 | Braun |
| 4,100,324 A | 7/1978 | Anderson et al. |
| 4,227,904 A | 10/1980 | Kasmark, Jr. et al. |
| 4,256,728 A | 3/1981 | Nishino et al. |
| 4,427,110 A | 1/1984 | Shaw, Jr. |
| 4,429,001 A | 1/1984 | Kolpin et al. |

(Continued)

FOREIGN PATENT DOCUMENTS

| | | |
|---|---|---|
| DE | 29900095 | 4/1999 |
| EP | 0 295 943 A2 | 12/1988 |
| EP | 0 389 015 A2 | 9/1990 |
| EP | 0 389 023 A2 | 9/1990 |
| EP | 0486006 A2 | 5/1992 |
| EP | 0 487 773 A1 | 6/1992 |
| EP | 0 269 462 B1 | 8/1992 |
| EP | 0 729 375 B1 | 9/1999 |
| EP | 1157672 A1 | 11/2001 |
| JP | 53-061559 | 6/1978 |
| JP | 55-064823 A2 | 5/1980 |
| JP | 58-079518 | 5/1983 |
| JP | 61-031162 | 2/1986 |
| JP | 1-011639 | 1/1989 |
| JP | 11-230665 A2 | 8/1999 |

(Continued)

OTHER PUBLICATIONS

International Search Report dated Aug. 29, 2002 for International Application No. PCT/US02/08519.

*Primary Examiner*—Krisanne Jastrzab
(74) *Attorney, Agent, or Firm*—Robert A. Ambrose

(57) ABSTRACT

A container liner, shelf liner or drawer liner that will absorb liquids spilled or leaked into a container or onto a shelf or drawer. The liner is a layered product having a layer which is impervious to liquids and an absorbent layer. The absorbent layer further contains a material which is capable of controlling odors, such as those odors found in refrigerators and waste receptacles. The liner of the present invention provides the benefit of absorbing spills and controlling odors in containers such as refrigerators and waste receptacles.

26 Claims, 3 Drawing Sheets

U.S. PATENT DOCUMENTS

| | | | |
|---|---|---|---|
| 4,469,734 A | 9/1984 | Minto et al. |
| 4,517,308 A | 5/1985 | Ehlenz et al. |
| 4,525,410 A | 6/1985 | Hagiwara et al. |
| 4,565,727 A | 1/1986 | Giglia et al. |
| 4,604,313 A | 8/1986 | McFarland et al. |
| 4,609,580 A | 9/1986 | Rockett et al. |
| 4,793,837 A | 12/1988 | Pontius |
| 4,795,482 A | 1/1989 | Gioffre et al. |
| 4,797,318 A | 1/1989 | Brooker et al. |
| 4,800,841 A | 1/1989 | Yananton et al. |
| 4,808,202 A | 2/1989 | Nishikawa et al. |
| 4,808,454 A | 2/1989 | Saitoh |
| 4,808,466 A | 2/1989 | Kotani et al. |
| 4,826,497 A | 5/1989 | Marcus et al. |
| 4,837,020 A | 6/1989 | Mise et al. |
| 4,865,596 A | 9/1989 | Weisman et al. |
| 4,868,032 A | 9/1989 | Eian et al. |
| 4,869,204 A | 9/1989 | Yananton |
| 4,886,697 A | 12/1989 | Perdelwitz, Jr. et al. |
| 4,900,377 A | 2/1990 | Redford et al. |
| 4,913,942 A | 4/1990 | Jick |
| 4,919,925 A | 4/1990 | Ueda et al. |
| 4,961,930 A | 10/1990 | Perdelwitz, Jr. et al. |
| 4,963,431 A | 10/1990 | Goldstein et al. |
| 5,022,553 A | 6/1991 | Pontius |
| 5,031,793 A | 7/1991 | Chen et al. |
| 5,046,604 A | 9/1991 | Forhetz et al. |
| 5,065,886 A | 11/1991 | Sher |
| 5,078,971 A | 1/1992 | Matuda et al. |
| 5,122,407 A | 6/1992 | Yeo et al. |
| 5,154,960 A | 10/1992 | Mucci et al. |
| 5,158,199 A | 10/1992 | Pontius |
| 5,161,686 A | 11/1992 | Weber et al. |
| 5,174,462 A | 12/1992 | Hames |
| 5,176,930 A | 1/1993 | Kannankeril et al. |
| 5,254,386 A | 10/1993 | Simpson et al. |
| 5,288,306 A | 2/1994 | Aibe et al. |
| 5,290,510 A | 3/1994 | Lee |
| 5,292,479 A | 3/1994 | Haraga et al. |
| 5,350,443 A | 9/1994 | von Blucher et al. |
| 5,360,654 A | 11/1994 | Anderson et al. |
| 5,415,779 A | 5/1995 | Markell et al. |
| 5,436,067 A | 7/1995 | Hanamoto et al. |
| 5,468,447 A | 11/1995 | Bermas |
| 5,468,536 A | 11/1995 | Whitcomb et al. |
| 5,486,410 A | 1/1996 | Groeger et al. |
| 5,492,675 A | 2/1996 | Brizard |
| H1579 H | 8/1996 | Furio |
| 5,567,231 A | 10/1996 | Yokoo et al. |
| 5,597,645 A | 1/1997 | Pike et al. |
| 5,611,486 A | 3/1997 | Paul |
| 5,641,561 A | 6/1997 | Hansen et al. |
| 5,647,881 A | 7/1997 | Zhang et al. |
| 5,720,832 A | 2/1998 | Minto et al. |
| 5,733,272 A | 3/1998 | Brunner et al. |
| 5,736,473 A | 4/1998 | Cohen et al. |
| 5,743,940 A | 4/1998 | Sugo et al. |
| 5,744,404 A | 4/1998 | Titterton et al. |
| 5,759,394 A | 6/1998 | Rohrbach et al. |
| 5,782,409 A | 7/1998 | Paul |
| 5,789,076 A | 8/1998 | Isohata |
| 5,799,909 A | 9/1998 | Ziegler |
| 5,858,515 A | 1/1999 | Stokes et al. |
| 5,885,681 A * | 3/1999 | Korpman ..................... 428/68 |
| 5,906,743 A | 5/1999 | Cohen et al. |
| 5,924,292 A | 7/1999 | Markum |
| 5,942,323 A | 8/1999 | England |
| 5,951,744 A | 9/1999 | Rohrbach et al. |
| 5,976,460 A | 11/1999 | Bourson et al. |
| 6,134,718 A | 10/2000 | Sesselmann |
| 6,156,086 A | 12/2000 | Zhang |
| 6,162,959 A | 12/2000 | O'Connor |
| 6,177,069 B1 | 1/2001 | Yokoyama et al. |
| 6,190,440 B1 | 2/2001 | Purnell |
| 6,203,810 B1 | 3/2001 | Alemany et al. |
| 6,214,095 B1 | 4/2001 | Logan et al. |
| 6,433,243 B1 * | 8/2002 | Woltman et al. ............ 604/359 |
| 6,509,284 B1 * | 1/2003 | Quincy et al. .............. 442/118 |
| 6,723,428 B1 * | 4/2004 | Foss et al. .................. 428/370 |

FOREIGN PATENT DOCUMENTS

| | | |
|---|---|---|
| JP | 00-111236 A2 | 4/2000 |
| WO | 91/12031 | 8/1991 |
| WO | 95/15187 | 6/1995 |
| WO | 97/02376 | 1/1997 |
| WO | 98/27919 | 7/1998 |
| WO | 00/20099 | 4/2000 |
| WO | 00/29209 | 5/2000 |
| WO | 00/29311 | 5/2000 |
| WO | 00/30599 | 6/2000 |
| WO | 00/39379 | 7/2000 |
| WO | 00/39380 | 7/2000 |
| WO | 00/50099 | 8/2000 |
| WO | 00/56523 | 9/2000 |
| WO | 00/73552 A1 | 12/2000 |
| WO | 01/15747 A1 | 3/2001 |
| WO | 01/21225 A2 | 3/2001 |
| WO | 01/30658 A1 | 5/2001 |

* cited by examiner

CONTAINER, SHELF AND DRAWER LINERS PROVIDING ABSORBENCY AND ODOR CONTROL

FIELD OF THE INVENTION

The present invention generally relates to an absorbent liner that provides odor control. More particularly, the present invention relates to absorbent liners that are used in locations where both odor control and liquid absorbency are needed, such as in refrigerators and cabinets, and around or in containers, such as, trash receptacles.

BACKGROUND OF THE INVENTION

Food and beverage spills in and around a kitchen will often present the problems of clean-up and odor control. This is especially true in refrigerators and waste receptacles in kitchens. Many times, a spill or a leak from a food or beverage container in a refrigerator goes unnoticed until the user of the refrigerator desires the item which has been spilled or which has leaked. By the time the item is desired, the spill or leak usually has solidified or has begun to solidify, leaving a hard to remove stain or residue on the refrigerator shelf or drawer. Often, this stain or residue will emit malodorous aromas into the refrigerator. The same is true for food stored in cabinets. Therefore, there is a need in the art to provide an effective means for absorbing such spills in refrigerators and cabinets and providing odor control.

Trash receptacles also present problems with liquid clean up. In the case of trash receptacles, a food or beverage containing bottle, can, jar, or resealable package, containing residual food or beverage is often thrown into a trash receptacle. This residual food or beverage content will often leak into the trash container. Most trash receptacles do not have an effective means for controlling leaks or spills of liquid food items. While plastic bags are often used to line a trash receptacle, many times these bags are damaged during installation, use or removal. In the case of a damaged plastic bag, any liquids in the plastic bag may leak into the trash receptacle. These liquids will often solidify or began to solidify leaving a residue, which may emit malodorous aromas. As will be recognized, the same issues are faced with disposal of nonconsumable trash, such as, for example, pet litter. Therefore, there is a need in the art to provide an effective liquid absorbing and odor control means in trash receptacles.

In addition, various foods stored in a refrigerator or cabinets often emit strong aromas. For example, aromas from garlic, cheeses, meats and/or spices will often permeate a refrigerator when these food items or dishes containing these food items are stored in a refrigerator, even for a short period of time. Many times, the aroma from one food item will blend with the aroma or flavor of another food item or overpower the aroma or flavor of another food item stored in the refrigerator. Likewise, spices and other food items, such as coffee, will often permeate a cabinet in which these items are stored. This often results in the wasting of food, due to the lost of flavor or appeal of a food item which has been overpowered by the aroma or flavor of another food item.

Many techniques have been employed to reduce this problem over the years. The most frequent technique is to carefully wrap food items, for example with plastic films, prior to storage in the refrigerator or cabinet. However, some odors or aromas from the wrapped food may still escape, due to various reasons, such as, incomplete wrapping, odors too strong to be effectively contained, or damage to the wrapping due to movement of food items in and out of the refrigerator and/or cabinet.

Other techniques used to reduce this problem include placing an open box of baking soda or other odor controlling substance in the refrigerator or cabinet. However, this technique presents the problem of spills of the contents of the open box into the refrigerator or cabinet, which may result in the contamination of food items stored in refrigerators or cabinets. Further, this technique of odor control is not effective in controlling spills or leaks in the refrigerator.

There are several other prior art odor adsorbing devices. For example, U.S. Pat. No. 5,046,604 to Forhetz et al. teaches an odor adsorbing liner that has pouches of odor adsorbing particles between two sheets. The pouches are prepared by stitching the sheets together in a quilt-type fashion. The sheets of material are disclosed as paper or cloth. The product of the '604 patent suffers from the problem that the odor absorbing particles are loose in the pouches and if one of the sheets becomes torn, the particles can be released into the refrigerator or cabinet. Further, the liners are difficult to cut to a specific size for a particular shelf or drawer since the areas containing the loose particles cannot be cut. If these sheets were cut in the pouch area, the loose particles in the pouch would no longer be contained within the pouch area, thereby causing the particles to be removed from the liner, which in turn will reduce the effectiveness of the odor adsorbing liner of the '604 patent.

In a similar manner, JP11-230665 teaches enveloping porous charcoal and carbon fibers with a nonwoven fabric. As with U.S. '604, enveloping of the active components presents the problem of the active particle becoming loose within the refrigerator.

Other prior art methods include placing a pouch of odor adsorbing particles into a device which hangs in a refrigerator shelf. Such devices are described in U.S. Pat. No. 5,772,959 to Bermas and U.S. Pat. No. 5,468,477 to Bermas. The odor adsorbing particles of these patents are sealed within a porous paper or a nonwoven polymeric felt. The device of these patents is effective in controlling odor within a refrigerator and/or cabinet, however, the device does not provide any means of controlling or managing spills which may occur within a refrigerator or cabinet.

In addition to the above-described methods, JP58-79518 discloses a refrigerator freshening device having an odor adsorbing material. The odor adsorbing material is a liquid absorber supported on a porous material. This odor adsorbing material is placed in a gas permeable film, wherein the film is impermeable to liquids. It is necessary for the film to be liquid impermeable since the liquid adsorber of the odor adsorbing material may leak from the device. As is clearly taught by JP '518, nonwoven materials are not suitable to contain the odor adsorber.

Attempts have been made in the art to control odors in containers, such as soiled diaper storage containers. U.S. Pat. No. 5,022,553 to Pontius discloses a nonwoven liner for a diaper container, wherein the nonwoven liner is impregnated with an odor adsorbing material. This patent, however, does not suggest that the nonwoven material is also capable of absorbing liquids.

Fibrous liquid absorbent pads are known in the art and have widely been used in personal care products, such as diapers, catamenial devices (tampons and sanitary napkins), incontinence pads and the like, to absorb bodily fluids. In recent years, various attempts have been made to impart odor control to these absorbent pads. See, for example, U.S. Pat. No. 4,826,497 to Marcus et al., U.S. Pat. No. 5,122,407 to Yeo et al., EP 0 515 473 to Procter & Gamble Company, EP 0 509 409 to Kimberly Clark Corporation and EP 0 389 015 to Procter & Gamble Company. Included in the methods suggested by these patents is the incorporation of odor adsorbing material in the formed articles. However, none of these patents suggest that a liner for a container, shelf or drawer can be made from these materials.

Further, fibrous absorbent pads have been used in a variety of other uses, such as bed pads (U.S. Pat. No. 4,650,481 to O'Conner), pet pads (U.S. Pat. No. 4,961,930 to Perdelwitz, Jr. et al), infant car seat pads( U.S. Pat. No. 4,886,697 to Perdelwitz, Jr. et al.) and floor covers or floor mats (U.S. Pat. No. 4,609,580 to Rockett et al.). Again, none of these patents suggest using the fibrous absorbent pads as a liner for a container, shelf or drawer.

SUMMARY OF THE INVENTION

Accordingly, an object of the present invention is to provide a container liner, shelf liner or drawer liner that can absorb liquids spilled or leaked into a container or onto a shelf or drawer.

Further, it is another object of the present invention to provide a container liner, shelf liner or drawer liner that can provide and maintain a fresh environment, without the disadvantage of the prior art shelf and drawer liners.

In addition, it is an object of the present invention to provide a container liner, a shelf liner or a drawer liner that can absorb spills of liquids while providing an odor neutralizing or controlling effect.

It is another object of the present invention to provide a disposable container liner, shelf liner or drawer liner that is cost efficient and can be easily disposed of upon absorbing a liquid or after the odor adsorbing material is no longer effective. The absorbent container liner, shelf liner or drawer liner of the present invention can simplify the clean up of such spills due to the absorbent and disposable nature of the liner of the present invention.

Another aspect of the present invention is to provide a method of controlling odors in a container. This aspect of the invention is achieved by placing the liner of the present invention into a container, such as a refrigerator, cabinet or trash receptacle.

An additional aspect of the present invention is to effectively increase the effective surface area of the odor controlling material as compared to other prior art odor controlling methods mentioned above.

DETAILED DESCRIPTION OF THE INVENTION

The liner of the present invention comprises a liquid impervious backing layer; and an odor controlling liquid absorbent layer comprising a stabilized matrix of thermoplastic fibers, an absorbent material and an odor controlling material.

As used herein, the term "stabilized matrix" means that the components of the matrix are essentially entrapped within the matrix, and only a very minor amount of the components of the matrix, if any, are capable of falling out of the matrix during handling and/or use.

The liner of the present invention is adapted for use as a liner for a container, a drawer or a shelf. As used herein, the term "container" means an object which is capable of holding other items. Examples of containers include, but are not limited to, refrigerators, cabinets, waste receptacles and boxes, etc. Given the liquid absorbing properties of the liners, the liners of the present invention are especially suited for containers which spills or leaks of liquids may occur. The liner of the present invention is especially adapted for use in a refrigerator drawer or bin and/or on a refrigerator shelf. As used herein, the term "refrigerator drawer" is intended to include, but not limited to, vegetable bins, meat storage bins and other such compartments commonly found in refrigerators. The liner of the present invention is also especially adapted to control odors the use environment, in addition to absorbing liquids.

As used herein, the term "polymer" generally includes, but is not limited to, homopolymers, copolymers, such as for example, block, graft, random and alternating copolymers, terpolymers, etc. and blends and/or modifications thereof. Furthermore, unless otherwise specifically limited, the term "polymer" shall include all possible spacial configurations of the molecule. These configurations include, but are not limited to, isotactic, syndiotactic and/or random symmetries.

As used herein, the phrase "odor controlling liquid absorbent layer" means a structure which has the ability to both absorb liquids and control, neutralize and/or adsorb odors.

Figure 1:
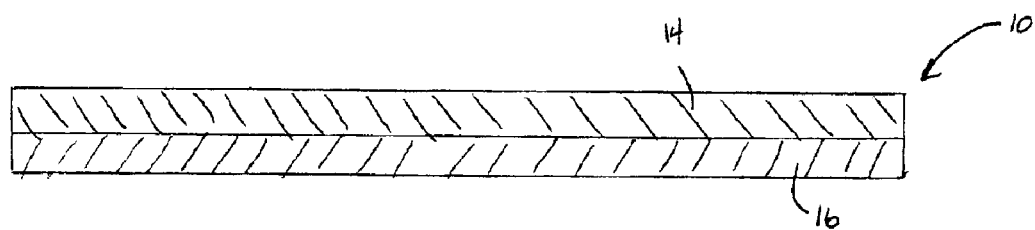
FIG. 1 is a cross-section for the liner of the present invention.

Illustrated in FIG. 1, the liner 10 of the present invention generally comprises at least two components, an odor controlling liquid absorbent layer 14 and a liquid impervious backing layer 16.

The odor controlling liquid absorbent layer 14, which may comprise one layer or a plurality of layers, is capable of absorbing liquids, such as, but not limited to, milk, sodas and other food related liquids. The odor controlling liquid absorbent layer 14 comprises a mixture of materials comprising thermoplastic fibers, an absorbent material and an odor controlling material.

The odor controlling liquid absorbent layer can comprise coform materials, although other suitable absorbent fabrics comprising a combination of thermoplastic fibers, an absorbent material and an odor controlling material may likewise be used in accord with the present invention. As used herein, the term "coform material" means composite materials comprising a mixture or stabilized matrix of thermoplastic fibers and a second non-thermoplastic material. As an example, coform materials may be made by a process in which at least one meltblown die head is arranged near a chute through which the non-thermoplastic material are added to the web while it is forming. The second non-thermoplastic material may be, for example, pulp, superabsorbent particles, cellulose fibers, staple fibers and other particles. In the present invention, the non-thermoplastic material is the combination of the absorbent material and the odor controlling material. Exemplary coform materials are disclosed in commonly assigned U.S. Pat. No. 5,284,703 to Everhart et al.; U.S. Pat. No. 5,350,624 to Georger et al.; and U.S. Pat. No. 4,100,324 to Anderson et al.; the entire content of each is incorporated herein by reference.

The thermoplastic fibers of the odor controlling liquid absorbent layer can be prepared from any thermoplastic polymer. Generally, the thermoplastic fibers are prepared from polyolefins, polyesters of polyamides. The most preferred polymer materials for the thermoplastic fibers of the absorbent layer are polyolefins, such as polyethylene and polyproplyene from the standpoint of cost and properties of the polyolefins. Typically, the thermoplastic fibers have a diameter up to about 15 microns, however, it is preferred that the diameter is between about 0.5 microns and about 10 microns.

Suitable absorbent materials include, but are not limited to, fibrous organic materials such as woody or non-woody pulp such as cotton, rayon, recycled paper, pulp fluff and also include inorganic absorbent materials such as superabsorbent materials and/or treated polymeric fibers. The absorbent materials may be used alone or in combination with other absorbent materials.

As used herein a "superabsorbent" or "superabsorbent material" refers to a water-swellable, water-soluble organic or inorganic material capable, under favorable conditions, of absorbing at least about 10 times its weight and, more desirably, at least about 20 times its weight in an aqueous solution containing 0.9 weight percent sodium chloride. Organic materials suitable for use as a superabsorbent material in conjunction with the present invention include, but are not limited to, natural materials such as guar gum, agar, pectin and the like; as well as synthetic materials, such as synthetic hydrogel polymers. Such hydrogel polymers include, for example, alkali metal salts of polyacrylic acids, polyacrylamides, polyvinyl alcohol, ethylene, maleic anhydride copolymers, polyvinyl ethers, methyl cellulose, carboxymethyl cellulose, hydroxypropylcellulose, polyvinylmorpholinone, and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. The superabsorbent materials may be in any form suitable for use in absorbent composites including particles, fibers, flakes, spheres and the like. Typically the superabsorbent material, when present, is present within the absorbent layer in an amount from about 5 to about 95 weight percent based on total weight of the absorbent body. Superabsorbents are generally available in particle sizes ranging from about 20 to about 1000 microns. Examples of suitable commercially available superabsorbents are SANWET IM 3900 available from Hoescht Celanese located in Portsmouth, Va. and DRYTECH 2035LD available from Dow Chemical Co. located in Midland, Mich.

The odor controlling liquid absorbent layer desirably has sufficient absorbent material to absorb at least about 1 gram of liquid per gram or and preferably about 3 grams to about 12 grams of liquid per gram of the liner, without the use of a superabsorbent. If a larger liquid capacity is desired or needed, the addition of the superabsorbent material will increase the absorbency of the liner.

In one embodiment, the odor controlling liquid absorbent layer 14 can comprise a coform material having a basis weight of at least about 35 gsm (grams per square meter), and more desirably comprises a coform material having a basis weight from about 70 gsm to about 340 gsm coform material. A coform material having a basis weight of about 70 gsm to about 180 gsm is most preferred.

Suitable odor controlling material of the odor controlling liquid absorbent layer can be any material known to those skilled in the art which will effectively control, neutralize and/or adsorb odor. Preferably, the odor controlling material is a solid material. Examples of such materials include, but are not limited to, baking soda (sodium bicarbonate), activated charcoal, activated carbon, clays, diatomaceous earths, and zeolites. These odor controlling materials can be used alone or in combination with one another. Typically, the loading of the odor controlling material is between about 2 gsm and about 80 gsm, depending of the basis weight of the absorbent layer. More preferably, the loading of the odor controlling material is between about 8 gsm and about 40 gsm; most preferably between about 12 gsm and 30 gsm. As with the absorbent material, the odor controlling material can be incorporated into the liquid absorbent layer using the coform process by adding an additional chute for the odor controlling material. On a percentage basis, the odor controlling material is generally present in an amount of about 0.5 to about 60% by weight of the odor controlling liquid absorbent layer. If the amount of the odor controlling material is below about 0.5% by weight, effective odor control may not be achieved. If the amount of the odor controlling material is more than about 60% by weight, additional odor controlling effects may not be observed. Further, if the amount of the odor controlling material present in the odor controlling liquid absorbent layer is above 60% by weight, the additional odor controlling material may be removed from the liner during handling, which creates the additional problem of clean-up of the dust resulting from the removal of the additional odor controlling agent from the liner. Preferably, the odor controlling material is between about 1 and about 40% by weight of the odor controlling liquid absorbent layer, and more preferably between about 5 and about 20% by weight.

The odor controlling liquid absorbent layer may also be prepared from other nonwoven fabrics or nonwoven webs. As used herein the term "nonwoven fabric" or "nonwoven web" means a web having a structure of individual fibers or threads which are interlaid, but not in an identifiable manner as in a knitted or meshed fabric. Nonwoven fabrics or webs have been formed from many processes such as for example, meltblowing processes, spunbonding processes, air-laid and bonded-carded web processes.

The odor controlling material could also be incorporated into the absorbent layer by other methods known to those skilled in the art. For example, the odor controlling material may be prepared in situ in the absorbent layer. As an example, the absorbent layer could be impregnated with liquid soda ash via various methods known to those skilled in the art. The soda ash could then be converted to sodium bicarbonate by immersing the treated absorbent layer in humid carbon dioxide. Other similar methods could be used to incorporated the odor controlling material in the absorbent layer.

In the meltblowing process, fibers are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. As used herein, the term "microfibers" means small diameter fibers having an average diameter not greater than about 10 microns. In a preferred embodiment the microfibers may have an average diameter of from about 0.5 microns to about 10 microns. Thereafter, the meltblown fibers are generally carried by the high velocity gas stream and are deposited on a collecting surface to form a web of randomly dispersed meltblown fibers. Such a process is disclosed, for example, in U.S. Pat. No. 3,849,241 to Butin et al. and U.S. Pat. No. 5,213,881 to Timmons et al.; the entire content of each is incorporated herein by reference. Meltblown fibers are often microfibers which can be continuous or discontinuous and are generally tacky when deposited onto a collecting surface.

In the spunbonding process, fibers are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman; U.S. Pat. No. 3,542,615 to Dobo et al.; and U.S. Pat. No. 5,382,400 to Pike et al.; the entire content of each is incorporated herein by reference Spunbond fibers are generally not tacky when they are deposited onto a collecting surface and thus often require additional mechanical or chemical bonding to form an integrated stabilized web.

As a further example, the absorbent material may be held in a web of thermoplastic staple fibers such as, for example, air-laid or bonded-carded webs. The liquid absorbent layer may comprise one or more layers and additional absorbent materials may be dispersed within the one or more layers to increase the absorbency as desired. Typically, the odor controlling material is adhered to the thermoplastic polymer of the odor controlling layer or are intertwined with thermoplastic polymer and the absorbent material, which results in the stabilized matrix of the present invention. As an example U.S. Pat. No. 4,784,892 to Storey et al. teaches an absorbent material of meltblown fibers with an absorbent fibrous material (e.g. wood pulp) as well as superabsorbent dispersed therein; the contents of the aforesaid patent is incorporated herein by reference. Other processes known to those skilled in the art can be used including the processes disclosed U.S. Pat. No. 4,469,734 to Minto et al., U.S. Pat. No. 5,720,832 to Minto et al. U.S. Pat. No. 4,797,318 to Brooker et al. and U.S. Pat. No. 4,429,001 to Koplin et al.; the contents of each is incorporated by reference in its entirety. In addition, the absorbent layer may comprise an absorbent layer of thermoplastic fibers and absorbent material wherein the weight percent of thermoplastic fibers to absorbent fibers to odor absorbing material varies through the depth of the fabric.

When the odor controlling material is held in place by the thermoplastic polymer or other method described in the above described U.S. patents, typically the odor controlling material is dispersed throughout the odor controlling liquid absorbent layer and the odor controlling material is prevented from dropping out of the layer. It is important to note that the efficacy of the odor controlling material is not and should not be adversely affected by the method in which the odor controlling material is held in the odor controlling liquid absorbent layer. It is this holding in place of the odor controlling material which allow the liner of the present invention to be cut to a desired shape without the loss of the odor controlling material from the portion of the liner to be used.

In the present invention, the preferred odor controlling liquid absorbent layer is a coform material. The coform material should preferably contain, taking into account only the absorbent material and thermoplastic fibers, between about 5% to about 70% by weight of thermoplastic fibers and about 95% to about 30% by weight of the absorbent material. More preferably, the coform material should contain, taking into account only the absorbent material and thermoplastic fibers, between about 10% to about 60% by weight of thermoplastic fibers and about 90% to about 40% by weight of the absorbent material.

The odor controlling liquid absorbent layer should comprise, taking into account the odor controlling material, thermoplastic fibers and absorbent material, about 1 to about 60% by weight odor controlling material, about 5% to about 70% by weight of thermoplastic fibers and about 94% to about 19% by weight of the absorbent material. More preferably, the coform material should contain, between about 1 to about 40% by weight of odor controlling material, about 10% to about 60% by weight of thermoplastic fibers and about 89% to about 25% by weight of the absorbent material. Most preferably, the odor controlling material should be about 5 to about 20% of the odor controlling absorbent layer. In one preferred embodiment, the odor controlling material is baking soda, the thermoplastic fiber comprises a polyolefin fiber, and the absorbent material comprises wood pulp. The preferred polyolefin is polypropylene.

The liquid impervious layer 16 may be any suitable material that is impervious to liquids. As used herein, the term "liquid impervious" means that a film, laminate or other fabric is relatively impermeable to the transmission of liquids, having a hydrohead of at least about 10 cm. Hydrohead as used herein refers to a measure of the liquid barrier properties of a fabric. The hydrohead test determines the height of water (in centimeters) which the fabric will support before a predetermined amount of liquid passes through. A fabric with a higher hydrohead reading indicates it has a greater barrier to liquid penetration than a fabric with a lower hydrohead. The hydrohead test can be performed according to Federal Test Method Standard 191A, Method 5514 or using a hydrostatic head tester available from Marlo Enterprises, Inc. of Concord, N.C. Unlike Method 5514, when using a hydrostatic head tester, the specimen is subjected to a standardized water pressure, increased at a constant rate until the first sign of leakage appears on the surface of the fabric in three separate areas. (Leakage at the edge, adjacent clamps is ignored.) Unsupported fabrics, such as a thin film, can be supported to prevent premature rupture of the specimen.

Typically, the impervious backing layer is prepared from a polymeric film. Examples of polymers which can be used to form the impervious film include, polymers and copolymers of olefins, nylon and polyesters. The actual polymer used to prepare the film is not critical to the invention. Given the disposable nature of the liner of the present invention, however, it is desirable to use polymer films having a low cost. Therefore, films of polyethylene or polypropylene are desired due to the low cost and reasonable strength provided by these polymers at an effective film thickness. Typically, the impervious layer has a thickness less than about 2 mils. The impervious layer preferably has a thickness between about 0.5 and about 1.5 mils.

In addition, the liquid impervious layer may be a multilayer nonwoven laminate which is relatively impervious to the transmission of liquids. As used herein "multilayer nonwoven laminate" means a laminate comprising a plurality of layers wherein at least one of the layers is a nonwoven fabric. As an example, laminates wherein some of the layers are spunbond and some meltblown such as a spunbond/ meltblown/spunbond (SMS) laminate and others as disclosed in U.S. Pat. No. 4,041,203 to Brock et al.; U.S. Pat. No. 5,169,706 to Collier et al.; U.S. Pat. No. 5,145,727 to Potts et al.; U.S. Pat. No. 5,178,931 to Perkins et al.; and U.S. Pat. No. 5,188,885 to Timmons et al.; the entire contents of which are incorporated herein by reference. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Multilayer laminates may also have various numbers of meltblown layers or multiple spunbond layers in many different configurations and may include other materials such as films (F), e.g. SMMS, SM, SF, SFS, etc.

The multilayered nonwoven laminate should have a hydrohead of at least about 10 cm or more and, even more desirably, has a hydrohead in excess of about 20 cm. In one embodiment, the multilayer nonwoven laminate can comprise a laminate of a first layer comprising at least a 6 gsm layer of thermoplastic polymer microfibers and a second layer comprising at least an 8 gsm layer of spunbond fibers; more desirably the multilayer laminate comprises from about 10 gsm to 25 gsm meltblown fibers and 15 gsm to about 34 gsm spunbond fibers. As used herein, the term "microfibers" means small diameter fibers having an average diameter not greater than about 10 microns. In a preferred embodiment the microfibers may have an average diameter of from about 0.5 microns to about 10 microns. Microfibers can include both meltblown fibers and/or fine spunbond fibers. With such a two layer laminate, the microfibers would preferably face the absorbent layer and the spunbond fibers should face the opposed outer or distal side of the liner. The liquid impervious layer may also include additional layers and desirably the total basis weight of the barrier laminate is less than about 102 gsm and even more desirably between about 20 gsm and about 68 gsm. In a further embodiment, the multilayer laminate can comprise a spunbond/meltblown/spunbond (SMS) laminate. Lower basis weight laminates, with good barrier properties such as disclosed in commonly assigned U.S. Pat. No. 5,492,751 to Butt et al., the entire content of which is incorporated herein by reference, are believed suitable for use in the present invention.

Preferably, the liquid impervious layer is a polyethylene film having a thickness in the range of about 0.5 mils to about 1.5 mils.

In order to help reduce slippage of the liner during use, an outer surface of the liquid impervious layer that will come into contact with the container, drawer or shelf desirable has a coarse, rough or tacky surface.

Figure 2:
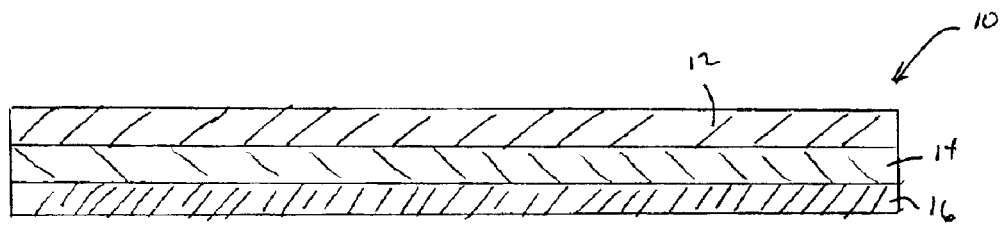
FIG. 2 is a cross-section for a liner of the present invention.

In addition to the liquid impervious layer and the odor controlling liquid absorbent layer, the liner may additionally contain a liquid pervious layer and which allows movement of the liquid away from its source to the absorbent layer. As used herein, the phrase "liquid pervious" is defined as a material that is permeable to liquids. When the liquid pervious layer is present, this structure of which is shown in FIG. 2, the layered structure is such that the odor controlling liquid absorbent material 14 is positioned between the liquid pervious layer 12 and the liquid impervious layer 16.

In order to retain the desired level of liquid permeability, the liquid pervious layer should have high void spacing and a basis weight less than about 70 gsm, preferably between about 5 gsm and 65 gsm, and most preferably between 10 gsm and 50 gsm. Desirably, the liquid pervious layer comprises a nonwoven web, such as, for example, continuous spunbond fiber webs, bonded/carded webs, staple fiber webs and/or hydroentangled webs. Suitable materials for the fibers of the liquid pervious layer include thermoplastic polymers such as polyolefins, polyamides (nylons), polyesters and copolymers and blends thereof.

The liquid pervious layer 12 may comprise either hydrophilic or hydrophobic material. Additionally, the liquid pervious layer can comprise both hydrophilic and hydrophobic components which desirably give the layer an overall hydrophilic character. As an example, the liquid pervious layer can comprise a nonwoven web comprising a mixture of hydrophilic and hydrophilic fibers. The liquid pervious layer preferably promotes transfer of liquid away from the outer surface of the liner to the absorbent layer. Preferably, the liquid pervious layer does not retain fluid.

Many thermoplastic polymers, including polyolefins, are inherently hydrophobic. Thus, in those instances where it is desired that the liquid pervious layer be hydrophilic, the fibers may require treatment to impart wettability or hydrophilic properties to the fibers. Methods of treating polymers to make them hydrophilic are disclosed in U.S. Pat. No. 4,920,168 to Nohr et al.; U.S. Pat. No. 3,973,068 to Weber; and U.S. Pat. No. 5,759,926 to Pike et al.; each is hereby incorporated by reference in its entirety. In addition, known surfactants, also known as wetting agents, can be used to impart wettability to the fibers, such as, for example, non ionic surfactant composed of a blend of sorbtan monooliate and ethoxylated hydrogenated castor oil which is commercially available under the tradename Ahcovel Base N62 from ICI America, Inc. Polyolefin fiber webs desirably comprise from about 2% to about 10% surfactant which is added to the polymer prior to extrusion. Once formed, the surfactant migrates to the surface of the fiber imparting wettability to the fiber.

In the present invention, it is preferred that a liquid pervious layer is present on the liner. It is further preferred that the liner is a spunbond layer. It is further preferred the polymer used to prepare the spunbond layer is a polyolefin, in particular, a polypropylene. It is further desirable that the polyolefin contains a wetting agent. As is stated above, this spunbond layer should have a basis weight of less than about 70 gsm and more preferably between about 10 gsm and about 50 gsm.

Figure 3:
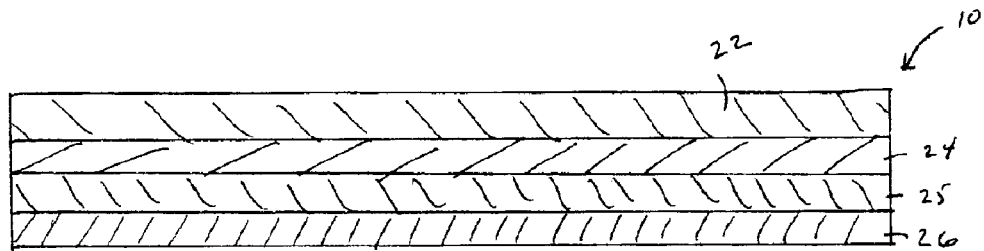
FIG. 3 is cross-section of a preferred embodiment of the present invention.
Figure 4:
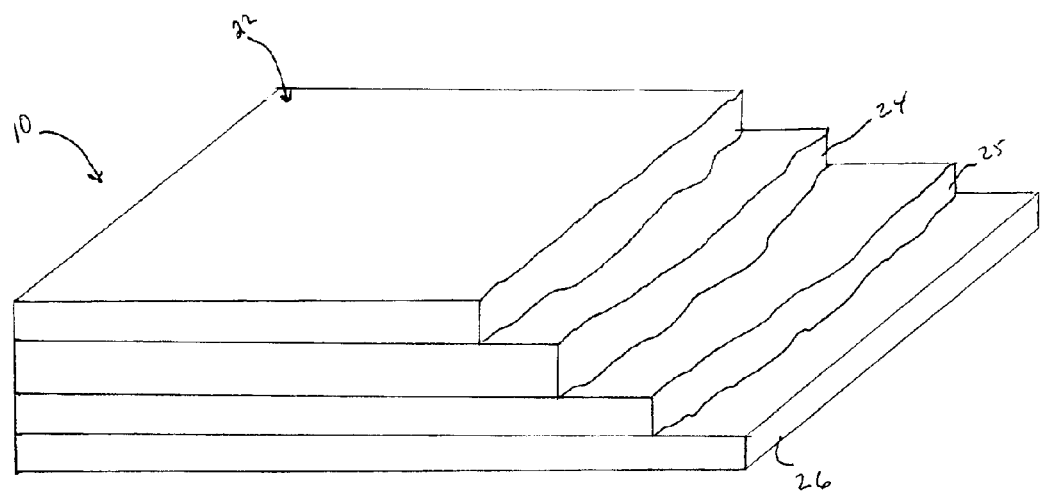
FIG. 4 is a perspective view of a preferred embodiment of the present invention.

A preferred aspect of the present invention is shown in FIG. 3. In FIG. 3, the liner 10 of the present invention is shown as a four-layer structure. A liquid pervious layer 22 is placed over two liquid absorbent layers 24 and 25. One or both of the liquid absorbent layers can contain the odor controlling material. However, if only one layer of the absorbent material contains the odor controlling material, it is preferred that the layer 25, which is adjacent to the liquid impervious layer 26, contains the odor controlling material. It is advantageous to have the odor controlling material in the absorbent layer distal to the top of the liner, since the odor controlling material may be soluble in the liquid absorbed by the liquid absorbent layer. With an additional absorbent layer above the layer containing the odor controlling material, containment of the fluid in which comes into contact with this layer may prevent from the liquid from coming into contact with the odor controlling material. This may allow the liner to still control odors even if the absorbent layer has come into contact with a liquid. Further, having the two layer structure gives the liner better fluid management.

Each of the absorbent layers can be made from different materials. In a preferred embodiment of the present invention, the absorbent layers are both are coform materials. It is further preferred that the layer 25 adjacent to the liquid impervious layer, hereinafter called the first layer 25, contains the odor controlling material and the layer 24 which is distal to the impervious layer, herein after called the second layer 24, does not contain the odor controlling material. In addition, it is preferred that the first layer 25 is a coform material which contains a thermoplastic fiber in the range of about 30–65% by weight, the absorbent material in the range of about 65–30% by weight, and about 1–40% by weight of the odor controlling material. The second layer 24 is preferably a coform material and contains about 10–40% by weight of thermoplastic fibers, and about 90–60% by weight of the absorbent material. In both of these layers, it is preferred that the thermoplastic polymer is a polyolefin and the absorbent material is wood pulp. It is further preferred that the odor controlling material is present in an amount of about 5 to about 20% by weight, based on the weight of the odor controlling material, the thermoplastic polymers, and the absorbent material in both layers 24 and 25. It is also preferred that the odor controlling material is baking soda.

In order to impart the densified areas to channel any spilled fluid away from the point of liner impact, the nonwoven web of fibers can be bonded such as, for example, comprising autogenously bonded webs or point bonded webs. Bonding can be accomplished by through-air bonding (TAB), thermal point bonding, ultrasonic bonding or other known bonding techniques. In order to improve the handling of the liner, point bonded fabrics desirably employ a repeating pattern of relatively small bond points. Employing such a pattern is believed to create a fabric texture more pleasing to the touch, i.e. with improved hand feel.

As used herein, the term "autogenous bonding" refers to bonding between discrete parts and/or surfaces independently of external additives such as adhesives, solders, mechanical fasteners and the like. As an example, multicomponent fibers may be autogenously bonded by through-air bonding whereby inter-fiber bonds develop at fiber contact points.

As used herein "point bonded" means bonding one or more fabrics with a pattern of discrete bond points. As an example, thermal point bonding often involves passing a fabric or web of fibers to be bonded between a pair of heated bonding rolls. One of the bonding rolls is usually, though not always, patterned in some way so that the entire fabric is not bonded across its entire surface, and the second or anvil roll is usually a smooth surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern, having generally alternating perpendicular segments, with about a 19% bond area. Typically, the percent bonding area varies from around 10% to around 30% of the area of the fabric laminate web. Point bonding may be used to hold the layers of a laminate together and/or to impart integrity to individual layers by bonding filaments and/or fibers within the web.

In another aspect of the present invention, the liquid pervious layer may be bonded in a pattern unbonded pattern. As used herein "pattern unbonded" or interchangeably "point unbonded" or "PUB", means a fabric pattern having continuous bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. An Example of a pub pattern is shown in FIG. 5.

Figure 5:
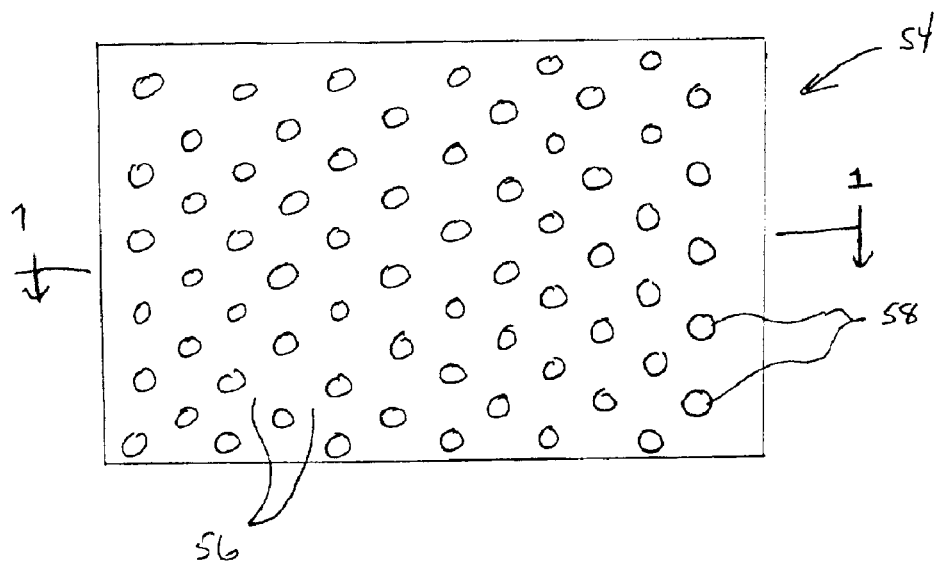
FIG. 5 is a top elevational view of the pattern-unbonded nonwoven fabric which can be used as a liquid pervious layer.
Figure 6:
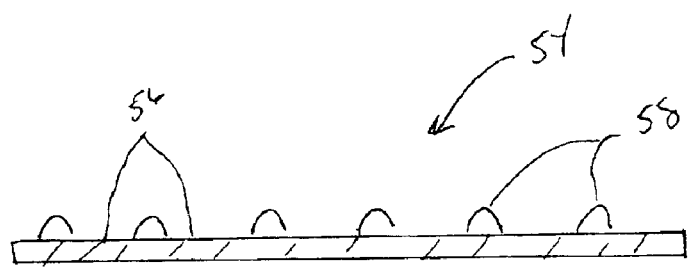
FIG. 6 is a cross-sectional side view of the pattern-unbonded fabric of FIG. 5 along section line 1—1 .

Referring to FIGS. 5 and 6, an embodiment of the pattern-unbonded nonwoven material 54 of the liquid pervious layer of the present invention is illustrated. The nonwoven fabric or web having continuous bonded areas 56 that define a plurality of discrete, dimensionally-stabilized unbonded areas 58. Within the continuous bonded areas 56, the fibers or filaments of the nonwoven web are thoroughly bonded or fused together, and desirably are non-fibrous, whereas within the unbonded areas 58, the fibers or filaments of the nonwoven fabric or web are substantially or completely free of bonding or fusing and retain their fibrous structure. It is pointed out that other shapes for the unbonded area other than circles can be used.

A suitable process for forming the pattern-unbonded nonwoven material of this invention includes providing a nonwoven fabric or web, providing oppposedly positioned first and second calender rolls and defining a nip there between, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web. The PUB pattern is further described in U.S. Pat. No. 5,858,515 to Stokes et al, the contents of which are hereby incorporated by reference.

The fibers or filaments used in making pattern unbonded nonwoven liquid pervious layer may have any suitable morphology and may include hollow or solid, straight or crimped, single component, conjugate or multicomponent fibers or filaments, and blends or mixes of such fibers and/or filaments, as are well known in the art. As used herein the term "multicomponent fibers" or "conjugate fibers" refers to fibers which have been formed from at least two polymers extruded from separate extruders but spun together to form one fiber. Bicomponent fibers refer to a common, specific class of multicomponent fiber wherein the fiber comprises two distinct components. The polymers are arranged in substantially constantly positioned distinct zones across the cross-section of the fibers and extend continuously along the length of the fibers. The configuration of such a fibers may be, for example, a sheath/core arrangement wherein one polymer is surrounded by another or may be a side-by-side arrangement, a pie arrangement or an "islands-in-the-sea" arrangement. Conjugate fibers are taught in U.S. Pat. No. 5,108,820 to Kaneko et al.; U.S. Pat. No. 4,795,668 to Krueger et al.; and U.S. Pat. No. 5,336,552 to Strack et al. Multicomponent fibers are also taught in U.S. Pat. No. 5,382,400 to Pike et al. and may be used to produce crimp in the fibers by drawing the multicomponent fibers with heated air; the entire contents of the aforesaid patent is incorporated herein by reference. For bicomponent fibers, the polymers may be present in ratios of 75/25, 50/50, 25/75 or any other desired ratios. The fibers may also have shapes such as those described in U.S. Pat. No. 5,277,976 to Hogle et al.; U.S. Pat. No. 5,466,410 to Hills; and U.S. Pat. Nos. 5,069,970 and 5,057,368 to Largman et al., which describe fibers with unconventional shapes.

Generally, it is preferred that the fibers used to prepare the PUB pattern are lofty in nature. However, it is important to note that the fibers are selected such that the liquid pervious layer promotes the transfer of the liquid away from the outer surface of the liner to the absorbent layer.

As a preferred embodiment when the liquid pervious layer is a material which has a patterned unbonded pattern, the fibers used to prepare liquid pervious nonwoven web are multicomponent thermoplastic fibers. Desirably the liquid pervious layer comprises a nonwoven web of bicomponent fibers such as, for example, fibers comprising a polyethylene polymer component and a polypropylene polymer component. One or more components of the multicomponent fibers of the liquid pervious nonwoven web can be hydrophilic.

All such nonwoven webs may be pre-bonded, using known nonwoven web bonding techniques such as the hot air knife, compaction rolls, through air bonding, ultrasonic bonding and stitchbonding, and subsequently bonded using the pattern-unbonded method, or alternatively, such nonwoven webs may only be bonded using the pattern-unbonded method.

In preparing the liner of the present invention, any method known to those skilled in the art can be used. For example, each nonwoven layer of the liner may be prepared by sequentially depositing nonwoven layer onto a moving belt. The process of U.S. patent application Ser. No. 09/419,039, filed Oct. 15, 1999 in the name of Riddell and which is commonly assigned to the assignee of the present invention, can be used to prepare the liner of the present invention. The entire contents of this patent application is hereby incorporated by reference. Alternatively, each nonwoven layer may be individually prepared, collected in rolls and combined in a subsequent bonding step. It is noted that when the liquid impervious layer is a film, it may be necessary to adhesively attach the film to the nonwoven layers. It is further noted that the method used to prepare the liner is not critical to the invention.

The multiple layers of the liner can be bonded together along the edge 42 of the liner 10. The multiple layers may be bonded such as, for example, by thermal bonding, ultrasonic bonding, mechanical crimping, stitching and/or adhesively bonded. Bonding the edges of the liner may prevent the liquid absorbed in the odor controlling liquid absorbent layer remain in this layer during use or remove of the liner in the use environment. In addition, bonding the edges of the liner may prevent any odor controlling material and/or absorbent material which may fall out of the stabilized matrix during shipping or handling of the liners from coming into contact with the use environment or the users of the liner. It is noted that it is not absolutely necessary for the edges to be bonded and many different bonding techniques may be used. If bonding of the edges is used, it may be advantages to bond the edge of the liner in such a way so that the liquid impervious layer cover the edges of the absorbent material.

From a processing standpoint, the most efficient and, therefore, a preferred way to bond the layers of the laminate together is to adhesively bond the layers to one another. The adhesives which can be used will be readily apparent to those skilled in the art and should be selected so that it will not lose its ability to hold the layers together in the use environment. For example, the adhesive holding the absorbent layer to the liquid impervious should not be water-soluble or lose tack under refrigerated conditions. Further, the adhesive should be selected should be a food grade adhesive, since the products of the present invention may be used in an environment which food will be present. Examples of such adhesives include Findley L8260. When applying the adhesive to the layer of the liner, care should be taken so that adhesive does not completely coat an absorbent layer or the liquid pervious layer. This may result in the liner not absorbing spilled liquids due to the formation of a film an upper surface of the absorbent layer. Methods are known to those skilled to prevent filming of an adhesive, such as using a patterned roll to apply the adhesive or lightly spraying the adhesive on a layer prior to attachment to another layer.

Bonding the individual layers of the absorbent liner to create a seal can be achieved by various means such as, for example, by bonding using thermal or ultrasonic energy in combination with pressure. However, it is important that the method of bonding does not destroy the overall purpose of the individual layers. As each of the layers includes thermoplastic polymers therein, bonding along an edge 42 acts to create a seal that reduces and/or prevents fluid from seeping out through the liner itself. The edge may be bonded, for example, with a continuous seam or a series of closely spaced point bonds. Desirably the bond or seal is positioned at the edge up to about 1 cm from the outermost edge of the liner and vice versa. In addition, it is also possible that the absorbent core not extend completely to the liner edge 42 such that the seal comprises a bond between the liquid impervious layer 16 and liquid pervious layer 12. Further, it is also possible that the liquid impervious layer wrap around the outside edge and over the liquid pervious layer.

The liner of the present invention has additional advantages when used in a refrigerator, in particular, the vegetable drawers. Since the liner of the present invention is capable of absorbing moisture, it also prolongs the life of fruits and vegetables stored. This is because moisture on the surface of fruits and vegetables tends to promote decay.

Fruits and vegetables continue to respire after they are harvested. This respiration is the oxidative breakdown of the sugars, starches, and organic acids to simpler molecules, including, but not limited to water and carbon dioxide, with energy released in the form of heat and metabolic energy. The rate of production of oxygen and carbon dioxide during respiration can be affected by altering certain of the characteristics of the atmosphere which surrounds the fruit or vegetable. For example, temperature and gaseous composition (e.g. oxygen, carbon dioxide, water and ethylene concentrations) are known to affect the rate of production of oxygen and carbon dioxide.

The major atmospheric variable affecting shelf life of fruits and vegetables is the relative humidity. If the relative humidity is too low transpirational damage occurs, which results in the loss of turgidity, e.g. wilting, which leads to desiccation, increased respiration, and ultimately, an unmarketable and inedible product. If the relative humidity is too high, moisture can condense on the fruit or vegetable. This leads to conditions favorable for microbial growth due to the presence of free water, which encourages the growth of bacteria and fungi, resulting in spoilage of the fruit or vegetable. The present invention provides a solution to the latter problem by absorbing liquid excess moisture from the refrigerator while maintaining relative humidity. In addition, any fruit or vegetable placed on the liner of the present invention will be less likely to form moisture on the surface in contact with the liner of the present invention, since the absorbent nature of the liner will cause such moisture to be absorbed into the liner.

In addition to placing a fruit or vegetable on the liner in a refrigerator drawer or on a refrigerator shelf, the liner may also be draped over the fruit or vegetable to help absorb moisture from upper surfaces of the fruit or vegetable not in contact with the liner. For example, a fruit or vegetable may be covered with portions of the liner which are not in use. This will assist in removing any condensation on the upper surfaces of the fruit or vegetable.

Using the PUB bonding pattern on the liquid pervious layer has some key advantages. The protrusions of the unbonded area elevates the fruit or vegetable in contact with the liner. That is, the fruit or vegetable is in contact with the protrusions of the PUB pattern and the fruit or vegetable is generally held above the bonded area of the PUB pattern. This allows for increased ventilation and/or vapor transfer underneath a fruit or vegetable. In addition, these protrusions provide an improved buffer between the absorbent layer and the fruit or vegetable which results in insulating the surface of the fruit or vegetable from the liquid moisture which has been absorbed by the liner. Stated another way, the protrusions help prevent the fruit or vegetable from coming into contact with the moisture absorbed by the liner, which may result in the reduction of the problems resulting from the contact of moisture with the surface of the fruit or vegetable.

The liner of the present invention can further contain effective amounts of scavengers for ethylene, carbon dioxide and oxygen incorporated in to the odor controlling liquid absorbent layer to assist in the control of these gases. Examples of these scavengers are known to those skilled in the art or will be readily apparent to those skilled in the art. Further, the liner of the present invention can contain a preservative, such as an antibacterial agent, a fungicide and other similar agents to prevent the growth of bacteria and/or fungus on a fruit or vegetable placed on the liner, or to prevent the growth of bacteria and/or fungus within the liner. Preferable, but not required, the preservative is placed in the absorbent layer. Suitable preservatives will be apparent to those skilled in the art.

Further, the liner of the present invention is very effective in absorbing meat juices that are often produced when meat is defrosted on a refrigerator shelf. Uncooked meat sometimes contains bacteria which is often destroyed during cooking. Many times, if bacteria are present in the meat, these bacteria will also be present in the meat juices. The liner of the present invention is designed to be a disposable product; therefore, the liner which has the absorbed meat juices can be thrown away after use, thereby reducing the chances that bacteria will contaminate other foods.

In addition to the above-disclosed uses of the liner of the present invention, it is noted that the liner can be used in any location which requires both liquid absorbency and odor control, for example on food counters in kitchens, shoe boxes, closets, pet beds, cat litter box liners and gym bags. Other possible uses will be apparent to those skilled in the art.

EXAMPLES

Example 1

Using the process describe in U.S. patent application Ser. No. 09/419,039, filed on Oct. 15, 1999, on a wettable polypropylene spunbond nonwoven fabric having a basis weight of 13.6 gsm (the liquid pervious layer) a first coform layer is formed. The first coform layer comprises 80% by weight pulp and 20% by weight polypropylene. A second coform layer comprising 60% by weight pulp and 40% by weight polypropylene and baking soda in an amount of 26 gsm is then formed on the first coform layer. The two layers of the coform material have a combined basis weight of 176 gsm, including the coform and backing soda. This three layer nonwoven web is then adhesively attached to a polyethylene film having a thickness of 1 mil. using a food grade adhesive. The polyethylene film is attached to the second coform layer which results in a four layer structure.

Example 2

Using the process describe in U.S. patent application Ser. No. 09/419,039, filed on Oct. 15, 1999, on a wettable spunbond nonwoven fabric prepared from a side-by-side bicomponent fiber, wherein one component of the fiber is polyethylene and the other component is polypropylene, having a basis weight of 42.4 gsm and a pattern unbonded bond pattern (the liquid pervious layer), a first coform layer is formed. The first coform layer comprises 80% by weight pulp and 20% by weight polypropylene. A second coform layer comprising 50% by weight pulp and 50% by weight polypropylene and baking soda in an amount of 26 gsm is then formed on the first coform layer. The two layers of the coform material have a combined basis weight of 176 gsm, including the coform and backing soda. This three layer nonwoven web is then adhesively attached to a polyethylene film having a thickness of 1 mil. using a food grade adhesive. The polyethylene film is attached to the second coform layer which results in a four layer structure.

While the invention has been described in detail with respect to specific embodiments thereof, and particularly by the examples described herein, it will be apparent to those skilled in the art that various alterations, modifications and other changes may be made without departing from the spirit and scope of the present invention. It is therefore intended that all such modifications, alterations and other changes be encompassed by the claims.

What is claimed is:

1. A liner adapted for use with a container, drawer or shelf to absorb spills of liquids and/or odor control within said container, drawer or on said shelf, said liner comprising
a liquid impervious backing layer; and
an odor controlling liquid absorbent layer comprising a stabilized matrix of thermoplastic fibers, an absorbent material and an odor controlling material;

wherein said liquid absorbent layer is a coform material comprising about 5% to about 70% by weight of the thermoplastic fibers, between about 94% to about 19% by weight of absorbent material and about 0.5% to about 60% by weight of odor controlling material.

2. The liner according to claim 1, further comprising a liquid pervious layer wherein the odor controlling liquid absorbent layer is positioned between the liquid pervious layer and the liquid impervious layer.

3. The liner according to claim 2, wherein the liquid pervious layer comprises a spunbond layer of polyolefin fibers, said polyolefin fibers further comprising a wetting agent.

4. The liner according to claim 1, wherein the absorbent material comprises wood pulp.

5. The liner according to claim 1, wherein the odor controlling material is selected from the group consisting of baking soda (sodium bicarbonate), activated charcoal, activated carbon, clays, diatomaceous earths, and zeolites.

6. The liner according to claim 5, wherein the odor controlling material comprises baking soda.

7. The liner according to claim 1, wherein the odor controlling liquid absorbent layer comprises a plurality of layers, each layer of the absorbent layer comprising thermoplastic fibers and an absorbent material, wherein at least one of the absorbent layers further comprises the odor controlling material.

8. The liner according to claim 7, wherein the odor controlling liquid absorbent layer comprises two layers, a first layer and a second layer, wherein the first layer is adjacent to the liquid impervious layer, said first layer comprises thermoplastic fibers, an absorbent material and the odor controlling; and the second layer is adjacent to the first layer and is distal to said liquid impervious layer.

9. The liner according to claim 8, further comprising a liquid pervious layer wherein the first and second absorbent layers are positioned between the liquid pervious layer and the liquid impervious layer.

10. The liner according to claim 9, wherein the liquid pervious layer comprises spunbond polypropylene, the thermoplastic fibers of the absorbent layers comprise polypropylene, the absorbent material comprises wood pulp, the odor controlling material comprises baking soda and the liquid impervious layer is a polyethylene film.

11. The liner of claim 1, wherein the odor controlling material is present in an amount of about 1% to about 40% by weight of the coform material.

12. The liner according to claim 8, wherein the first layer is a coform material comprising thermoplastic fibers in the range of about 30–65% by weight and the absorbent material in the range of about 65–30% by weight end about 1–40% by weight of the odor controlling material; and the second layer is a coform material comprising thermoplastic fibers in an amount of about 10–40% by weight and the absorbent material in the range of about 90–60% by weight.

13. The liner according to claim 12, wherein the odor controlling material comprises about 5–20% by weight of the total weight of the first and second layers, taking into account the total weight of the odor controlling material, the thermoplastic polymers, and the absorbent material present in both the first and second layer.

14. The liner according to claim 13, further comprising a liquid pervious layer positioned adjacent to said second layer, distal to said first layer.

15. The liner according to claim 14, wherein the liquid pervious layer comprises spunbond polypropylene, the thermoplastic fibers of the absorbent layers comprises polypropylene, the absorbent material comprises wood pulp, the odor controlling material comprises baking soda and the liquid impervious layer comprises a polyethylene film.

16. The liner of claim 1, wherein the odor controlling liquid absorbent layer further comprises an ethylene scavenger, an oxygen scavenger, a carbon dioxide scavenger, a fungicide or an antibacterial agent.

17. The liner of claim 2, wherein the liquid pervious layer has a point unbonded bond pattern.

18. The liner of claim 17, wherein the liquid pervious layer is prepared from multicomponent fibers.

19. A container comprising the liner of claim 1.

20. A refrigerator comprising the liner of claim 1.

21. A trash receptacle comprising the liner of claim 1.

22. A shelf comprising the liner of claim 1, wherein the liner is positioned on an upper surface of the shelf.

23. A drawer comprising the liner of claim 1, wherein the liner is positioned inside the drawer.

24. A method of controlling odor and/or spills of a liquid in a container, drawer or on a shelf, said method comprising placing odor controlling liquid absorbent liner in said container, drawer or on a shelf, an odor controlling liquid absorbent liner comprising liquid impervious backing layer; and
an odor controlling liquid absorbent layer comprising a mixture of thermoplastic fibers, an absorbent material and an odor controlling material;

wherein said liquid absorbent layer is a coform material comprising about 5% to about 70% by weight of thermoplastic fibers, between about 94% to about 19% by weight of absorbent material and about 0.5% to about 60% by weight of odor controlling material and further wherein said liquid absorbent odor controlling layer is positioned between said liquid pervious outer layer and said liquid impervious backing layer.

25. The method of claim 24, wherein said container is a refrigerator and said liner is placed on an upper surface of a shelf or in a drawer of said refrigerator.

26. The method of claim 24, wherein said container is a waste receptacle.

* * * * *